United States Patent [19]

Kanno et al.

[11] Patent Number: 4,884,133
[45] Date of Patent: Nov. 28, 1989

[54] ENDOSCOPE LIGHT SOURCE APPARATUS

[75] Inventors: Masahide Kanno; Hisao Yabe; Takeshi Yokoi, all of Hachioji; Jun Yoshinaga, Hino; Kazuhiko Ohzeki, Hachioji, all of Japan

[73] Assignee: Olympus Optical Co., Ltd., Tokyo, Japan

[21] Appl. No.: 204,312

[22] Filed: Jun. 9, 1988

[30] Foreign Application Priority Data

Jun. 11, 1987 [JP] Japan ................. 62-145526

[51] Int. Cl.$^4$ .................. A61B 1/04; A61B 1/06
[52] U.S. Cl. ................................ 358/98; 128/6
[58] Field of Search ............... 358/98; 128/6

[56] References Cited

U.S. PATENT DOCUMENTS 4,638,353  1/1987  Nagasaki ................. 358/98

FOREIGN PATENT DOCUMENTS 60-217327  10/1985  Japan .

Primary Examiner—Howard W. Britton
Attorney, Agent, or Firm—Armstrong, Nikaido, Marmelstein, Kubovcik & Murray

[57] ABSTRACT

The endoscope light source apparatus of this invention can be selectively connected with an endoscope having a light guide means which can transmit an illuminating light for an object and an endoscope having a light source which can illuminate an object. The endoscope connected to the endoscope light source apparatus is discriminated by a scope discriminating circuit outputting a signal which can control a light guide light source and a power source which can feed an electric power to the light source provided in the endoscope.

7 Claims, 14 Drawing Sheets

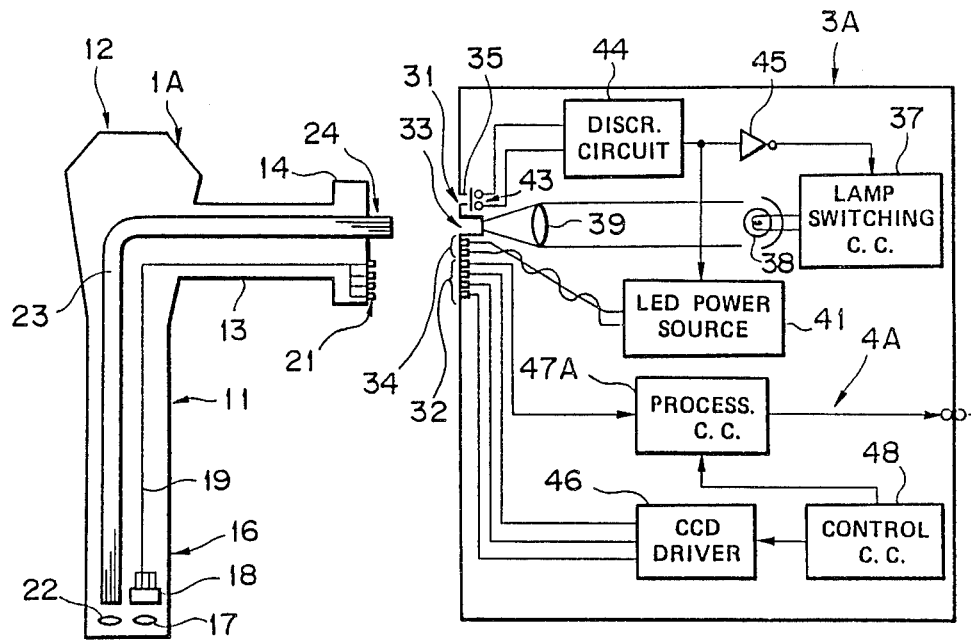
FIG. 1(b)
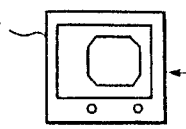
FIG. 1(a)
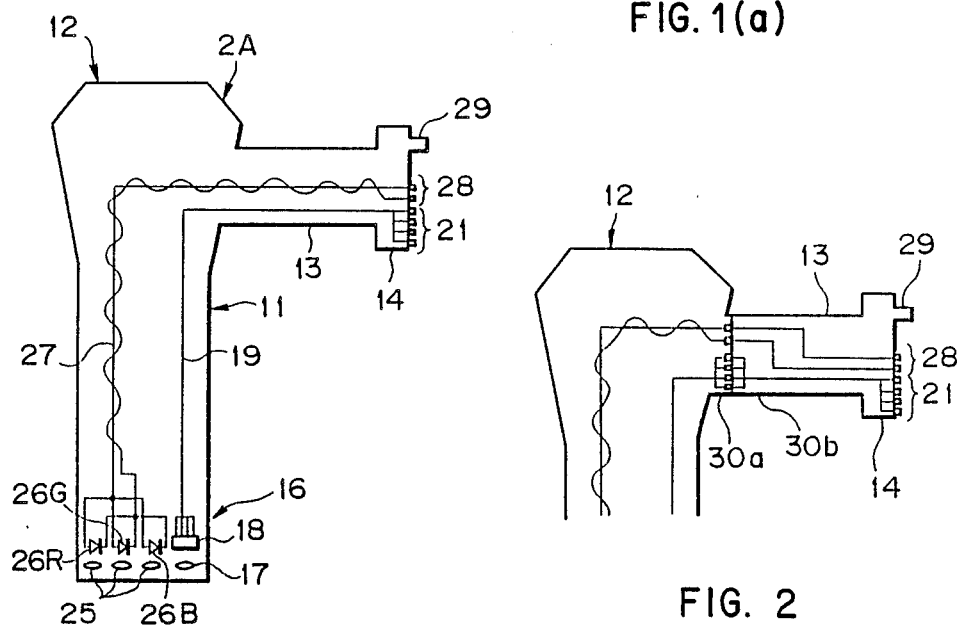
FIG. 1(c)
FIG. 2

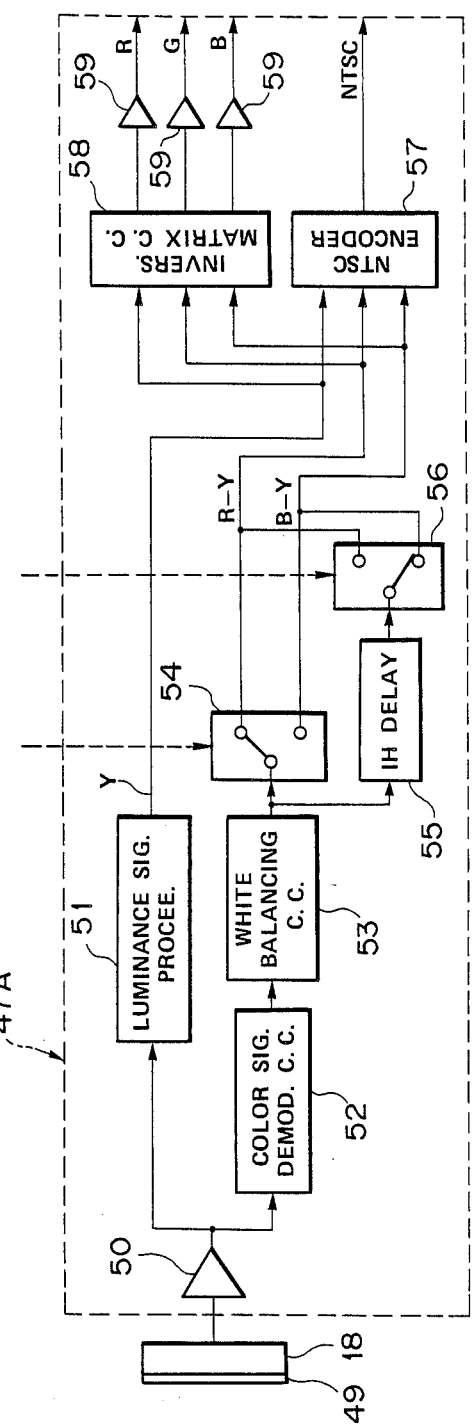
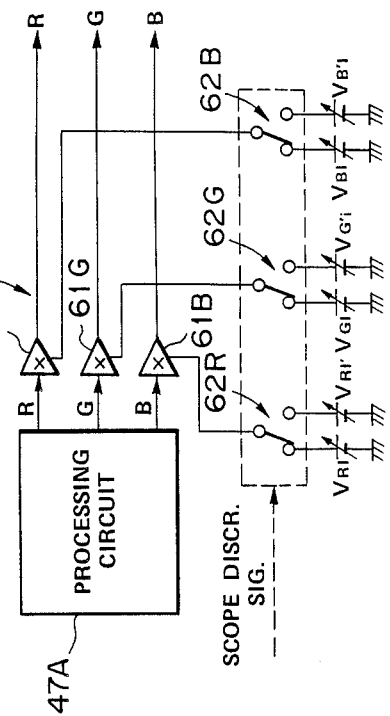

← DARK PICTURE → ← BRIGHT PICTURE →

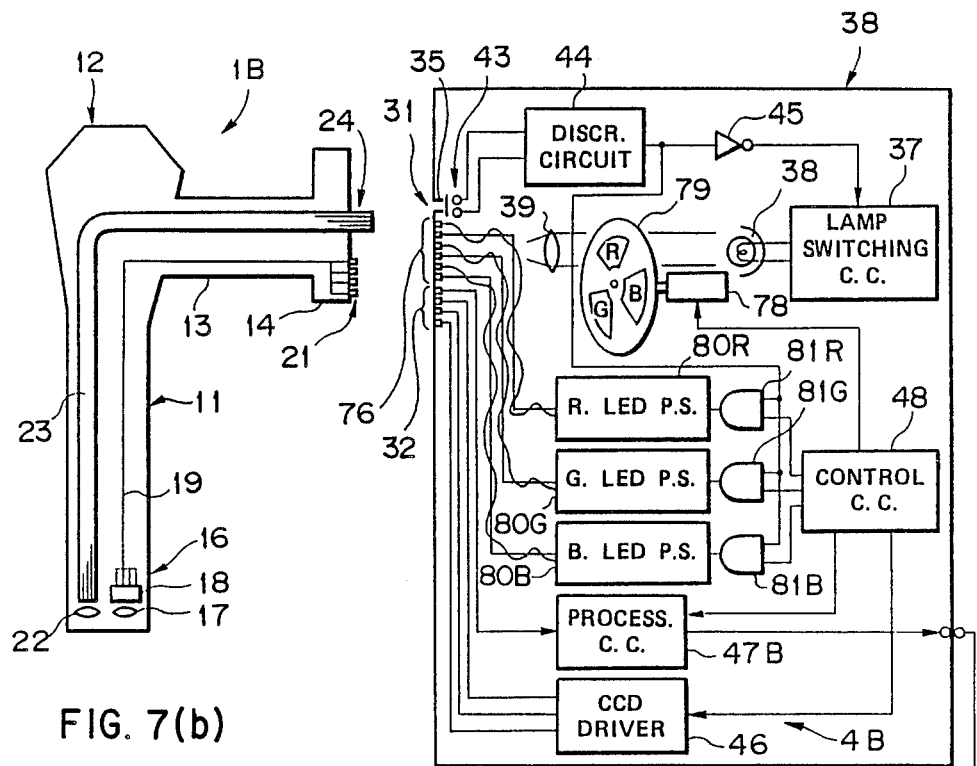
FIG. 7(b)
FIG. 7(a)
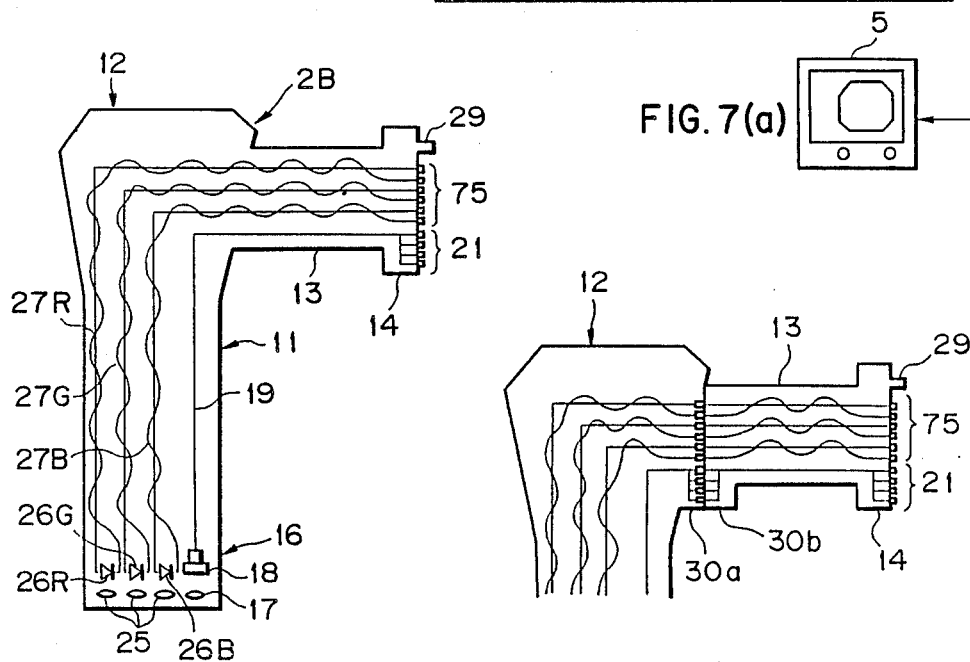
FIG. 7(c)
FIG. 8

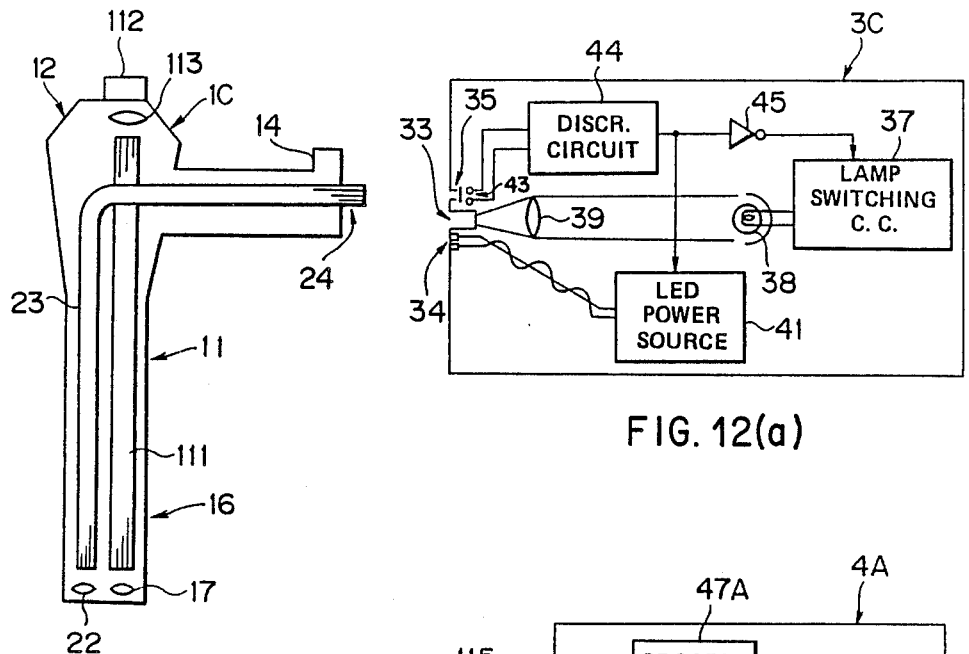
FIG. 12(a)
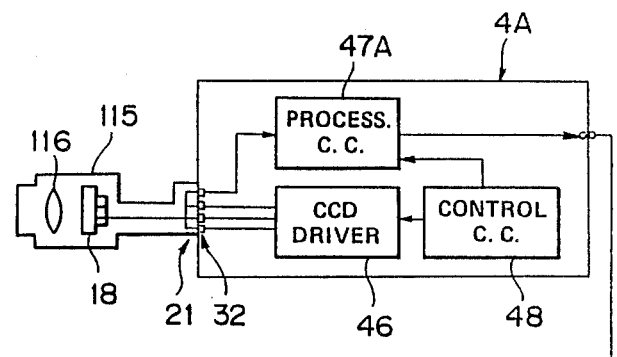
FIG. 13
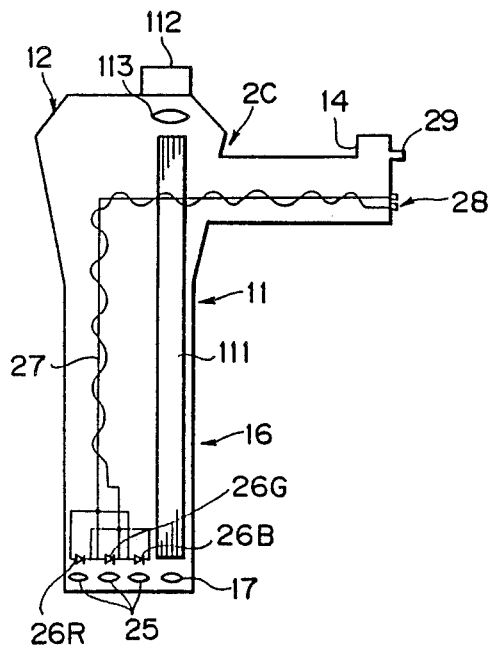
FIG. 12(b)
FIG. 12(c)

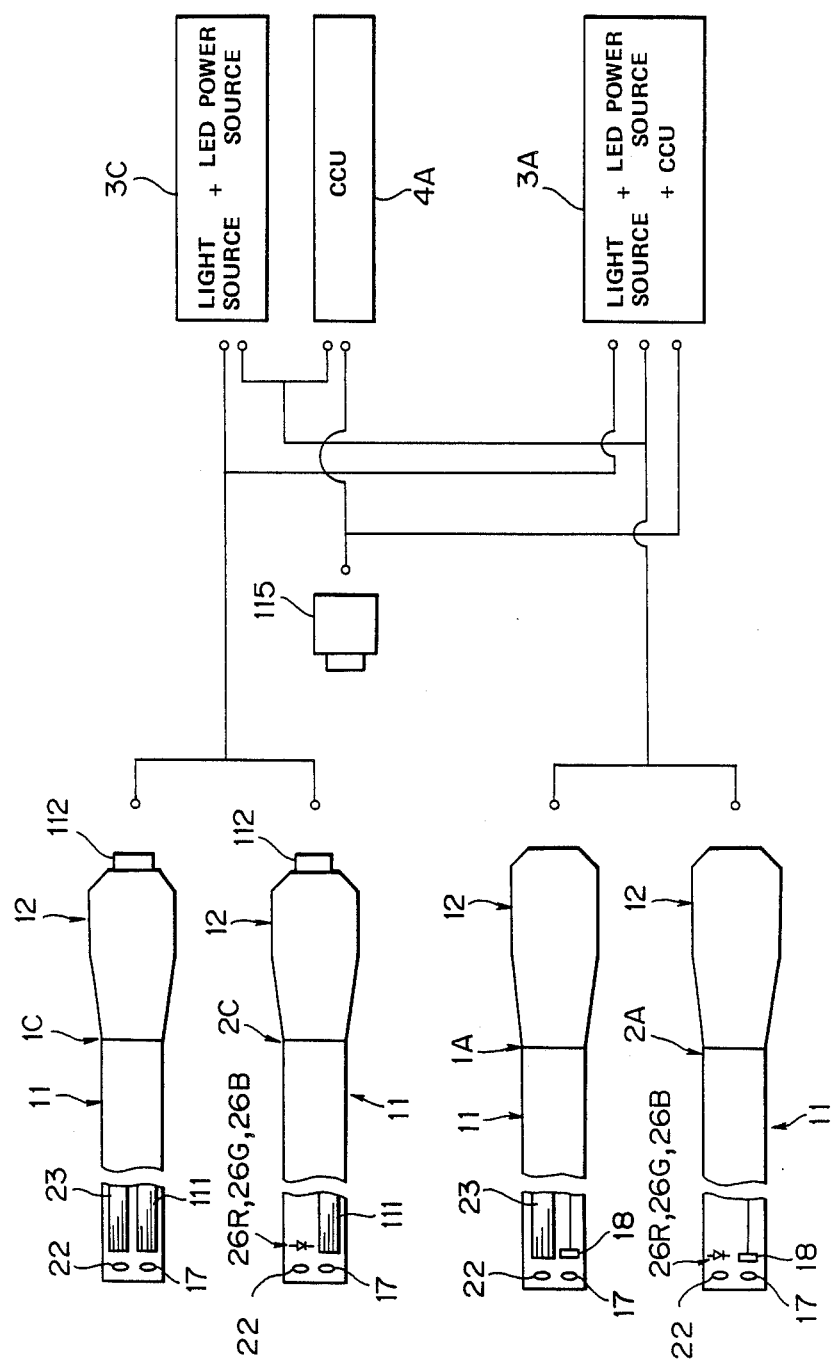

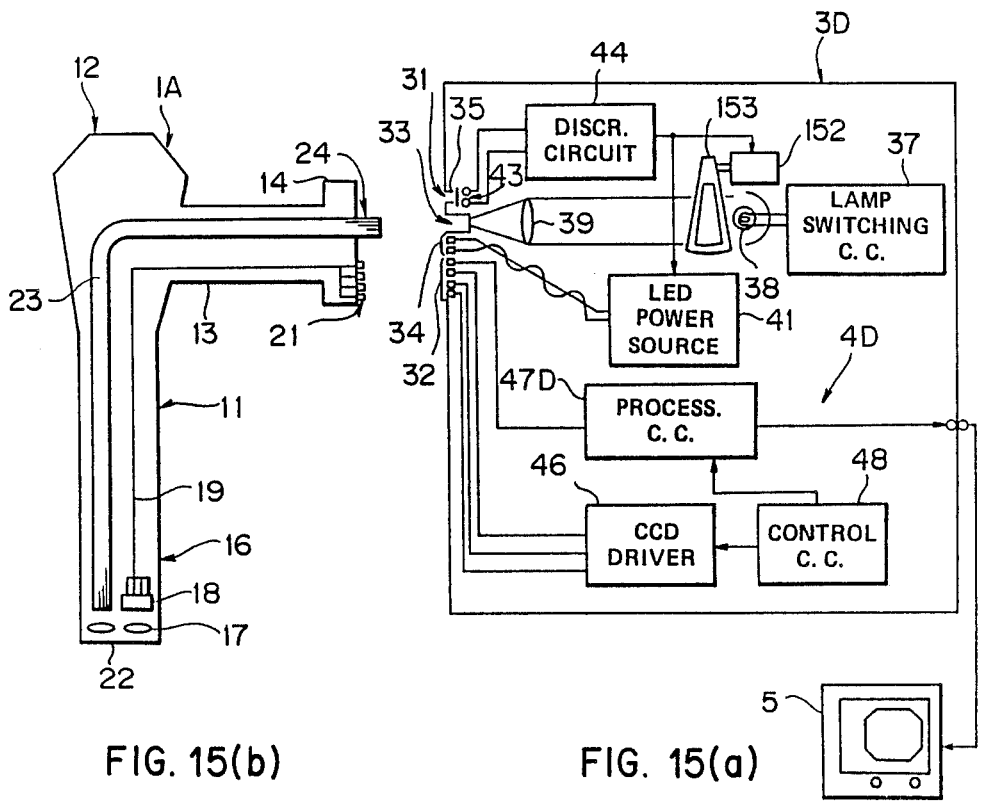
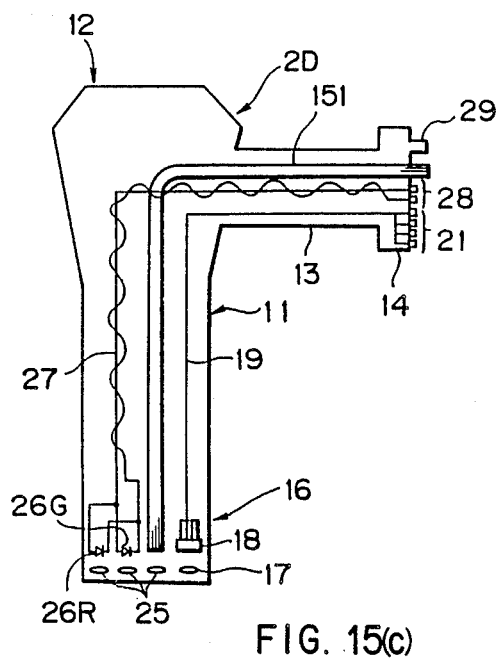
FIG. 15(b)   FIG. 15(a)
FIG. 15(c)

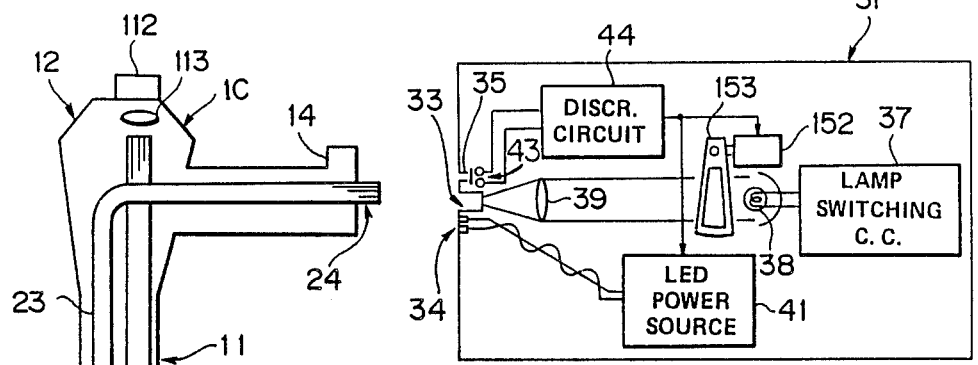
FIG. 20(a)
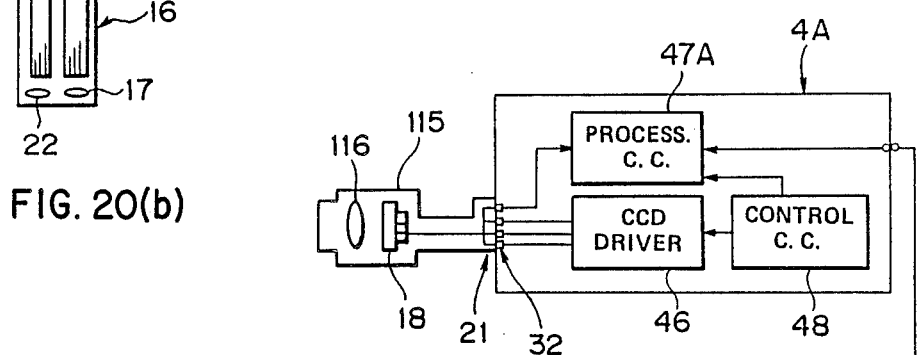
FIG. 20(b)
FIG. 21
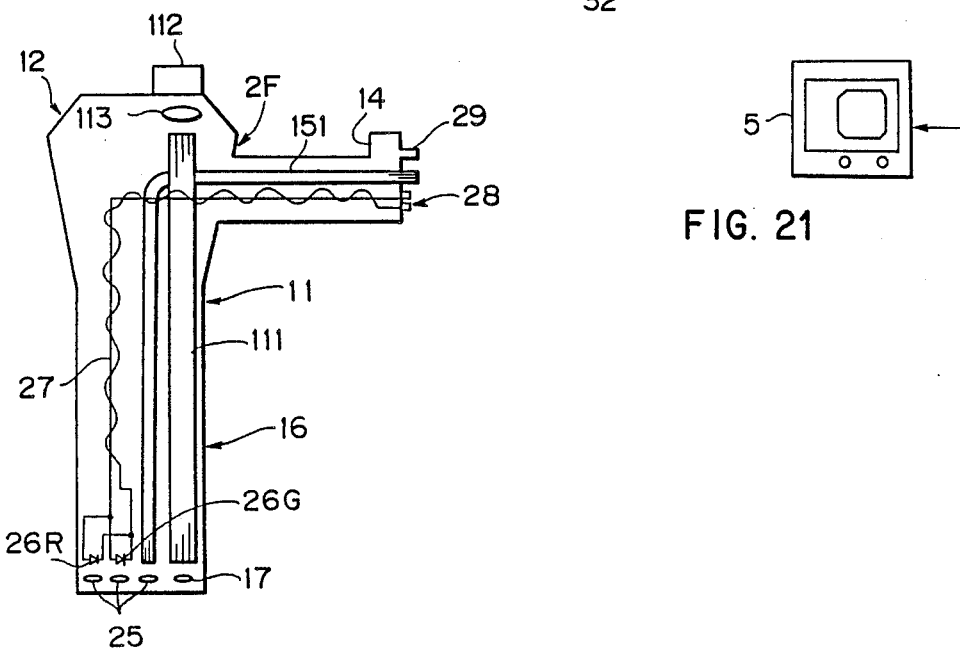
FIG. 20(c)

ENDOSCOPE LIGHT SOURCE APPARATUS

FIELD OF THE INVENTION

This invention relates to an endoscope light source apparatus which can be used in common by both an endoscope having a light guide and an endoscope having a light source.

BACKGROUND OF THE INVENTION

Recently, there is extensively used an endoscope whereby organs within a body cavity can be observed by inserting an elongate insertable part into the body cavity and, as required, various curing treatments can be made by using treating tools inserted through a treating tool channel.

There are also suggested various electronic endoscopes (called also electronic scopes) wherein a solid state imaging device such as a charge coupled device (CCD) is used as an imaging means.

Now, in the above mentioned endoscope, there has been conventionally an illuminating light feeding means, as largely divided, wherein a light guide is inserted through the endoscope insertable part and an illuminating light from the light source apparatus is fed to this light guide and wherein a lamp such as a light emitting diode (abbreviated as LED hereinafter) is provided in the tip part of the endoscope and is made to emit a light.

The endoscope having the above mentioned light guide has advantages that the tip part of the insertable part can be made fine, the light emitted from the light source apparatus can be variously changed and the observation with a special wavelength illuminating light, such as an infrared light for an electronic endoscope, is easy.

On the other hand, the endoscope having a lamp in the tip part has advantages that the flexible part connected to the rear end of the above mentioned tip part can be made fine, the light guide will not break and, even if the insertable part is long, it will not become dark.

Now, the endoscope having the light guide and the endoscope having the lamp have been used a respectively separately connected to the light source apparatus and to the power source. Therefore, in case the above mentioned two kinds of endoscopes are to the used, respectively different light source apparatuses and power source will have to be prepared and operated. Thus, the economy and efficiency have been low.

In the publication of a Japanese patent application laid open No. 217327/1985, there is disclosed a technique that a red color LED and blue color LED slightly containing a green component are provided at the tip of an endoscope insertable part. An object image obtained from illuminating lights emitted from these LED's is imaged by a solid state imaging device having a mosaic filter. The output signal of the solid state imaging device is separated into respective color component signals of red, green and blue and then further the color component signals are amplified so that the color characteristics of the reproduced picture image may be uniform.

OBJECT AND SUMMARY OF THE INVENTION

An object of the present invention is to provide an endoscope light source apparatus which can be used in common by both an endoscope having a light guide and an endoscope having a light source emitting an illuminating light.

The endoscope light source apparatus according to the present invention is provided with a light source feeding an illuminating light to the light guide of an endoscope having a light guide and a power source feeding an electric power to a light source internally provided in an endoscope so that the illuminating light ma be fed to the endoscope having the light guide and the electric power may be fed to the endoscope having the light source.

The other features and advantages of the present invention will become apparent with the following explanation.

BRIEF DESCRIPTION OF THE DRAWINGS

FIGS. 1 to 6 relate to the first embodiment of the present invention.

FIG. 1 (a) is an explanatory view showing the formation of a light source apparatus.

FIG. 1 (b) is an explanatory view showing an electronic scope fitted with an LG (light guide).

FIG. 1 (c) is an explanatory view showing an electronic scope fitted with an LED (light emitting diode) at the tip.

FIG. 2 is an explanatory view showing a modification of the tip LED fitted electronic scope.

FIG. 3 is a block diagram showing the formation of a video signal processing circuit.

FIG. 4 is an explanatory view showing the formation of a spectral intensity correcting circuit.

FIG. 5 is an explanatory view showing the formation of a light adjusting circuit.

FIG. 6 is a waveform view showing the operation of the light adjusting circuit.

FIG. 7 to 11 relate to the second embodiment of the present invention.

FIG. 7 (a) is an explanatory view showing the formation of a light source apparatus.

FIG. 7 (b) is an explanatory view showing an LG fitted electronic scope.

FIG. 7 (c) is an explanatory view showing a tip LED fitted electronic scope.

FIG. 8 is an explanatory view showing a modification of the tip LED fitted electronic scope.

FIG. 9 is a block diagram showing the formation of a video signal processing circuit.

FIG. 10 is an explanatory view showing the formation of a spectral intensity correcting circuit.

FIG. 11 is an explanatory view showing the formation of a light adjusting circuit.

FIG. 12 to 14 relate to the third embodiment of the present invention.

FIG. 12 (a) is an explanatory view showing the formation of a light source apparatus.

FIG. 12 (b) is an explanatory view showing an LG fitted filter scope.

FIG. 12 (c) is an explanatory view showing a tip LED fitted filter scope.

FIG. 13 is an explanatory view showing the formation of an externally fitted television camera and CCU (camera control unit).

FIG. 14 is an explanatory view showing an endoscope system to which this embodiment is applied.

FIG. 15 and 16 relate to the fourth embodiment of the present invention.

FIG. 15 (a) is an explanatory view showing the formation of a light source apparatus having a blue color filter.

FIG. 15 (b) is an explanatory view showing an LG fitted electronic scope.

FIG. 15 (c) is an explanatory view showing an electronic scope having a tip LED and LG.

FIG. 16 is an explanatory view showing the formation of a light adjusting circuit.

FIG. 17 (a) is an explanatory view showing the formation of a light source apparatus.

FIG. 17 (b) is an explanatory view showing an LG fitted electronic scope.

FIG. 17 (c) is an explanatory view showing an electronic scope having a tip LED and LG.

FIG. 18 is a timing chart view for explaining the operation of a lamp lighting circuit.

FIG. 19 is an explanatory view showing the formation of a light adjusting circuit.

FIGS. 20 and 21 relate to the sixth embodiment of the present invention.

FIG. 20 (a) is an explanatory view showing the formation of a light source apparatus.

FIG. 20 (b) is an explanatory view showing an LG fitted electronic scope.

FIG. 20 (c) is an explanatory view showing a scope having a tip LED, LG and IG.

FIG. 21 is an explanatory view showing the formation of an externally fitted television camera and CCU (camera control unit).

DETAILED DESCRIPTION OF PREFERRED EMBODIMENT

Figure 5:
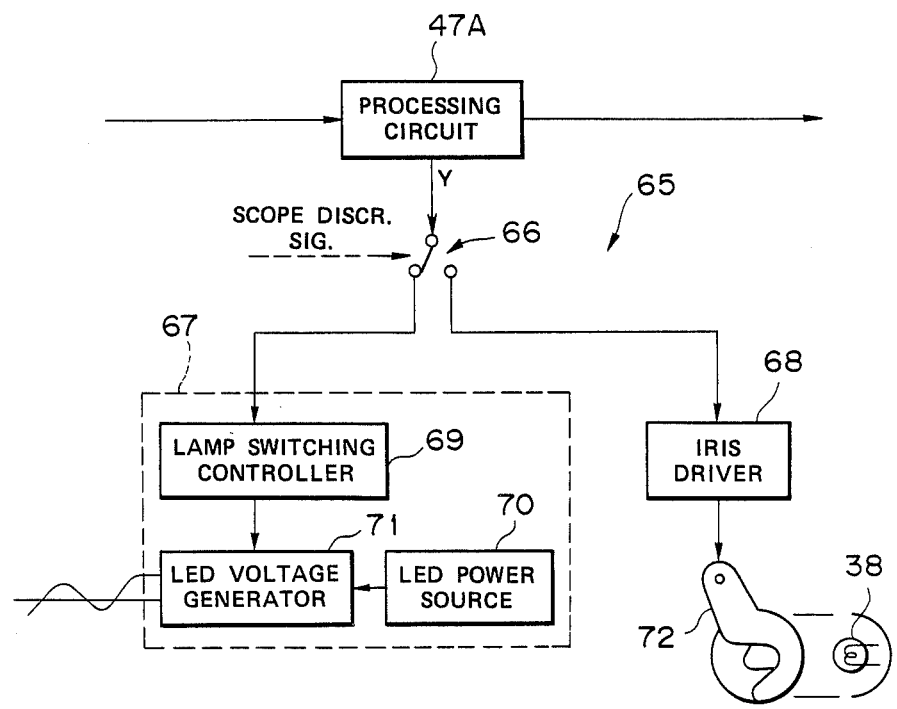

FIGS. 1 to 6 show the first embodiment of the present invention.

In this embodiment, as shown in FIG. 1 (a), there is provided a light source apparatus 3A common to an electronic scope (mentioned as an LG fitted electronic scope hereinafter) 1A having a light guide transmitting an illuminating light as is shown in FIG. 1 (b) and an electronic scope (mentioned as a tip LED fitted electronic scope hereinafter) 2A provided with an LED for a lamp in the tip part of the insertable part as is shown in FIG. 1 (c). In this embodiment, a simultaneous type is used for a color imaging system in each of the above mentioned electronic scopes 1A and 2A. The above mentioned light source apparatus 3A contains a camera control unit (mentioned as a CCU hereinafter) 4A corresponding to this simultaneous type. A color monitor 5 is to be connected to the above mentioned light source apparatus 3A.

As shown in FIGS. 1 (b) and (c), each of the above mentioned electronic scopes 1A and 2A is provided with an elongate, for example, flexible insertable part 11 to the rear end of which a thick operating part 12 is connected. A flexible universal cord 13 is extended sidewise from the above mentioned operating part 12 and is provided at the tip with a connector 14 to be connected to the above mentioned light source apparatus 3A. An objective lens system 17 is provided in the tip part 16 of the above mentioned insertable part 11. A solid state imaging device as, for example, a CCD 18, is arranged in the image forming position of this objective lens system 17. A color filter array, in which a color filter transmitting respectively color light of red (R), green (G), blue (B), etc. (not illustrated) which are arranged like a mosaic, is provided on the front surface of the light receiving surface of the above mentioned CCD 18. A signal line 19 is connected to the above mentioned CCD 18, is inserted through the above mentioned insertable part 11 and universal cord 13 and is connected to a signal connector 21 of the above mentioned connector 14.

As shown in FIG. 1 (b), in the above mentioned LG fitted electronic scope 1A, a light distributing lens 22 is provided in the above mentioned tip part 18 and a light guide (LG) 23 made, for example, of a fiber bundle and transmitting an illuminating light is provided on the rear end side of this light distributing lens 22, is inserted through the above mentioned insertable part 11 and universal cord 13 and is connected to a light source connector 24 of the above mentioned connector 14.

On the other hand, as shown in FIG. 1 (c), in the above mentioned tip LED fitted electronic scope 2A, three light distributing lenses 25 are provided in the above mentioned tip part 18 and a red color light emitting LED 26R, green color light emitting LED 266 and blue color light emitting LED 26B are arranged respectively on the rear end sides of the respective light distributing lenses 25 and are connected, for example, in parallel with a cable 27 inserted through the above mentioned insertable part 11 and universal cord 13 and connected to a power source connector 28 of the above mentioned connector 14. A scope discriminating switch pressing part 29 is provided to project on the above mentioned connector 14.

For the above mentioned tip LED fitted electronic scope 2A, inserted through the above mentioned universal cord 13 are only the signal line 19 and cable 27. Therefore, as shown in FIG. 2, the operating part 12 may be provided with a connector receptacle 30 and the universal cord 13a may be provided with a connector 30b to be connected with the above mentioned connector receptacle 30a so that the above mentioned universal cord 13 may be removably fitted to the operating part 12.

As shown in FIG. 1 (a), the light source apparatus 3A common to both the above mentioned electronic scopes 1A and 2A is provided with a connector receptacle 31 connectable with both connectors 14 of the above mentioned electronic scopes 1A and 2A and provided with a signal connector receptacle 32 to be connected with the signal connectors 21 of the above mentioned electronic scopes 1A and 2A, a light source connector receptacle 33 to be connected with the light source connector 24 of the above mentioned LG fitted electronic scope 1A, a power source connector receptacle 34 to be connected with the power sources connector 28 of the above mentioned tip LED fitted electronic scope 2A and an engaging hole 35 to be engaged with the switch pressing part 29 of the above mentioned tip LED fitted electronic scope 2A.

A light source lamp 38 emitting a white color light and controlled in lighting by a lamp lighting circuit 37 is provided within the above mentioned light source apparatus 3A. The illuminating light emitted out of this light source lamp 38 will be condensed by a condenser lens 39, will enter the entrance end of the light guide 23 of the light source connector 24 of the above mentioned LG fitted electronic scope 1A to be connected to the above mentioned light source connector receptacle 33, will be led to the tip part 16 by the above mentioned light guide 23, will be emitted out of the exit end and will be radiated onto an object through the light distributing lens 22.

An LED lighting power source 41 is provided within the above mentioned light source apparatus 3A, is connected to the above mentioned power source connector receptacle 34 and is connected to the above mentioned respective LED 26R, 26G and 26B through the power source connector 28 and cable 27 of the tip LED fitted electronic scope 2A to be connected to the above mentioned power source connector receptacle 34 to feed an electric power to them. By the electric power fed by the above mentioned LED lighting power source 41, the above mentioned respective LED 26R, 26G and 26B will respectively simultaneously emit a red color light, green color light and blue color light which will be radiated onto the object through the light distributing lenses 25. This object will be illuminated by a white color light by the composition of the above mentioned respective color lights.

A scope discriminating switch 43 is provided on the inner side of the above mentioned engaging hole 35 so that, when the switch pressing part 29 of the above mentioned tip LED fitted electronic scope 2A is engaged with the above mentioned engaging hole 35, this switch 43 will be pressed by this switch pressing part 29 to be on. A scope discriminating circuit 44 discriminating the type of the scope connected to the connector receptacle 31 by discriminating the on-off state of the above mentioned switch 43 is provided within the above mentioned light source apparatus 3A. By this discriminating circuit 44, when the above mentioned switch 43 is on, it will be discriminated that the tip LED fitted electronic scope 2A is connected and, for example, an H level discriminating signal will be output but, on the other hand, when the above mentioned switch 43 is off, it will be discriminated that the LG fitted electronic scope 1A is connected or nothing is connected and, for example, an L level discriminating signal will be output.

The discriminating output of the above mentioned scope discriminating circuit 44 will be input as a power source on-off signal without being inverted into the above mentioned LED lighting power source 41 and as a lamp lighting/extinguishing signal as inverted by an invertor 45 into the above mentioned lamp lighting circuit 37.

Therefore, when the tip LED fitted electronic scope 2A is connected to the above mentioned connector receptacle 31, the above mentioned LED lighting power source 41 will be on but, on the other hand, when the LG fitted electronic scope 1A is connected to the above mentioned connector receptacle 31 or nothing is connected, the above mentioned lamp lighting circuit 37 will be on.

A CCU (camera control unit) 4A is contained in the above mentioned light source apparatus 3A and is provided with a CCD driving circuit 46 applying driving pulses to the CCD 18 of the electronic scope 1A or 2A, a video signal processing circuit 47A processing the output signals of the above mentioned CCD 18 to be video signals and a control circuit 48 controlling the timing, etc. of the above mentioned CCD driving circuit 46 and video signal processing circuit 47A. The above mentioned CCD driving circuit 46 and video signal processing circuit 47A are connected to the above mentioned signal connector receptacle 32 and are connected to the CCD 18 through this signal connector receptacle 32, the signal connector 21 of the scope 1A or 2A connected to this signal connector receptacle 32 and the signal line 19. The above mentioned CCD 18 is driven by driving pulses from the above mentioned CCD driving circuit 46. The signals read out of this CCD 18 are processed by the above mentioned video signal processing circuit 47A to be video signals. The video signals from this video signal processing circuit 47A are input into the color monitor 5 and the object image is displayed in this color monitor 5.

The above mentioned video signal processing circuit 47A is formed, for example, as shown in FIG. 3.

That is to say, a color filter array 49 in which color filters transmitting respectively color light of R,G and B are arranged like a mosaic or the like is provided on the front surface of the CCD 18. The signals read out of the above mentioned CCD 18 will be amplified by a pre-amplifier 50 and will be input into a luminance signal processing circuit 51 and color signal reproducing circuit 52. A luminance signal Y will be produced in the above mentioned luminance signal processing circuit 51. Color difference signals R-Y and B-Y will be produced in time series in each horizontal line in the above mentioned color signal reproducing circuit 52, will be compensated in the white balance by a white balance circuit 53 and will be input on one side directly into an analogue switch 54 and will be delayed on the other side by one horizontal line by a 1H delay line 55 and will be input into an analogue switch 56 to obtain color difference signals R-Y and B-Y respectively from the above mentioned anologue switches 54 and 56. The above mentioned luminance signal Y and color difference signals R-Y and B-Y will be input into an NTSC encoder 57, will be converted to a composite video signal of an NTSC system and will be output. Also, the above mentioned luminance signal Y and color difference signal R-Y and B-Y will be input into an inverse matrix circuit 58, will be converted to color signals R, G and B and will be output as three primary color signals R, G and B through drivers 59.

The white color illuminating light in the LG fitted electronic scope 1A emitted from the light source lamp 38 and transmitted by the light guide 23 and the white color illuminating light in the tip LED fitted electronic scope 2A made by composing the respective color lights emitted from the respective LED 26R, 26G and 26B are different from each other in the spectral intensity in some case. Therefore, such illuminating light spectral intensity correcting circuit 60 may be provided.

In this illuminating light spectral intensity correcting circuit 60, the R, G and B color signals from the video signal processing circuit 47A will be input respectively into multipliers 61R, 61G and 61B and will be adjusted in the gain respectively independently by the multipliers 61R, 61G and 61B. The multiplied amount setting terminals of the above mentioned respective multipliers 61R, 61G and 61B are connected respectively to the fixed contacts of two-contact switching switches 62R, 62G and 62B. Variable voltage power sources $V_{R1}$, $V_{R1'}$, $V_{G1}$, $V_{G1'}$ and $V_{B1}$ and $V_{B1'}$ and connected respectively to the switching contacts of the respective switching switches 62R, 62G and 62B. The above mentioned switching switches 62R, 62G and 62B are switched as operatively connected by scope discriminating signals from the scope discriminating circuit 44 so that, when the LG fitted electronic scope 1A is COnnected, the power source $V_{R1}$, $V_{G1}$ and $V_{B1}$ sides will be respectively selected and, when the tip LED fitted electronic scope 2A is connected the power sources $V_{R1'}$, $V_{G1'}$ and $V_{B1'}$ will be respectively selected. Therefore, with the above mentioned LG fitted electronic scope 1A and tip LED fitted electronic scope 2A, the gain by the above mentioned multipliers 61R, 61G and 61B will be switched.

When the color signals R, G and B after the spectral intensity is corrected by the above mentioned illuminating light spectral intensity correcting circuit 60 are converted to a luminance signal Y and color difference signals R-Y and B-Y and are input into the NTSC encoder, a composite video signal of the NTSC system in which the spectral intensity is corrected will be able to be obtained.

A light adjusting circuit 65 as is shown, for example, in FIG. 5 may be also provided.

In this light adjusting circuit 65, a luminance signal Y from a video signal processing circuit 47A will be selectively input into an LED lighting circuit 67 and an iris driving circuit 68 through a switching switch 66. The above mentioned switch 66 will be switched by a scope discriminating signal from the scope discriminating circuit 44 so that, when the tip LED fitted electronic scope 2A is connected, an LED lighting circuit 67 side will be selected and, when the LG fitted electronic scope 1A is connected, a iris driving circuit 68 side will be selected.

Figure 6:
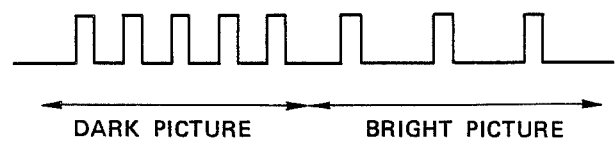
Figure 9:
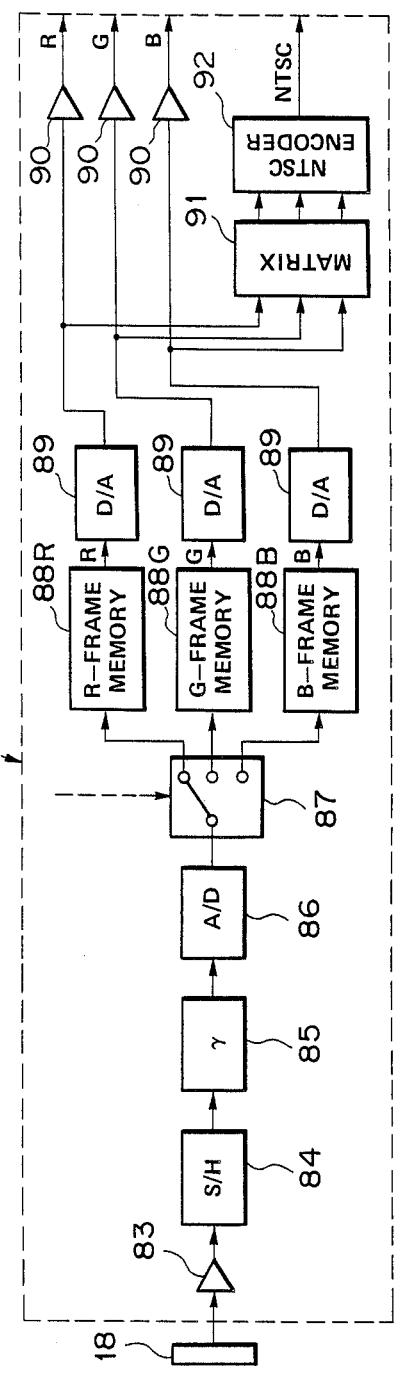

The above mentioned LED lighting circuit 67 comprises a lighting time number controlling circuit 69 wherein the above mentioned luminance signal Y is input and the number of times of lighting the LED per unit time is controlled in response to the level of this luminance signal Y, and LED lighting power source 70 and an LED lighting voltage generating circuit 71 connected to the above mentioned LED lighting power source 70, controlled by the above mentioned lighting time number controlling circuit 69 and generating a voltage, for example, like pulses applied to the LED. In the above mentioned lighting time number controlling circuit 69, when the level of the luminance signal Y is small, that is, when the image is dark, the number of lighting times will be increased and, on the other hand, when the level of the luminance signal Y is large, that is when the image is bright, the number of lighting times will be decreased. Therefore, as shown in FIG. 6, the waveforms of the LED lighting voltage output from the above mentioned LED lighting voltage generating circuit 71 will be short pulses in the period when the image is dark but will be long pulses in the period when the video image is bright.

On the other hand, in the above mentioned iris driving circuit 68, in response to the level of the luminance signal Y, a mechanical iris 72 arranged on the light path of the light source lamp 38 will be driven and the illuminating light amount will be adjusted to be of a proper exposure.

Thus, in this embodiment, the light source lamp 38 feeding an illuminating light to the light guide 23, the LED lighting power source 41 feeding an electric power to the LED 26R, 26G and 26B and the CCU 4A are provided within the light source apparatus 3A.

Therefore, by providing one light source apparatus 3A, both of the LG fitted electronic scope 1A and tip LED fitted electronic scope 2A can be used.

Further, by the scope discriminating circuit 44, the type of the connected scope can be discriminated and the illuminating light or electric power adapted to the connected scope can be automatically fed and therefore the operatability will be improved.

The conventional light source apparatus or power source apparatus containing a CCU is separately provided for each of the LG fitted electronic scope 1A and tip LED fitted electronic scope 2A and therefore two CCU's 4 are provided. However, according to this embodiment, the CCU 4A is rise in common by the LG fitted electronic scope 1A and tip LED fitted electronic scope 2A and therefore the cost will be reduced.

In this embodiment, the lamp lighting circuit 37 and LED lighting power source 41 may be manually switched to be on/off without providing the scope discriminating circuit 44.

FIGS. 7 to 11 show the second embodiment of the present invention.

This embodiment is used with a frame sequential type color imaging system.

In this embodiment, an LG fitted electronic scope 1B and tip LED fitted electronic scope 2B correspond to the frame sequential type and a color filter array is provided on the front surface of the CCD 18. The other formations of the above mentioned LG fitted electronic scope 1B are the same as the LG fitted electronic scope 1A in the first embodiment. In the above mentioned tip LED fitted electronic scope 2B, as shown in FIG. 7 (c), cables 27R, 27G and 27B are connected respectively to the red color light emitting LED 26R, green color light emitting LED 26G and blue color light emitting LED 26B and are connected to a power source connector 75 of the connector 14. The other formations are the same as the tip LED fitted electronic scope 2A in the first embodiment.

Even in this embodiment, in the case of the above mentioned tip LED fitted electronic scope 2B, inserted through the universal cord 13 are only the signal line 19 and cables 27R, 27G and 27B. Therefore, as shown in FIG. 8, the operating part 12 may be provided with the connector receptacle 30a and the universal cord 13 may be provided with the connector 30b to be connected to the above mentioned connector receptacle 30a so that the above mentioned universal cord 13 may be removably fitted to the operating part 12.

On the other hand, as in the first embodiment, the light source apparatus 3B of this embodiment has a connector receptacle 31 provided with the signal connector receptacle 32 to be connected with the signal connector 21 of the above mentioned electronic scope 1B and 2B a light source connector receptacle (not illustrated) to be connected with the light source connector 24 of the above mentioned LG fitted electronic scope 1B and a power source connector receptacle 76 to be connected with a power source connector 75 of the above mentioned tip LED fitted electronic scope 2B.

Within the above mentioned light source apparatus 3B, a rotary filter 79, having filters transmitting three color lights of R, G and B and rotated and driven by a motor 78, is arranged in front of the light source lamp 38. The white color light emitted from the above mentioned light source lamp 38 will be illuminating light of the respective wavelengths sequentially of R, G and B through the above mentioned rotary filter 79, will then be condensed by the condenser lens 39 and will enter the entrance end of the light guide 23 of the light source connector 24 of the above mentioned LG fitted electronic scope 1B connected with the above mentioned light source connector receptacle. The above mentioned motor 78 is controlled in rotation by the control circuit 48.

Also, within the above mentioned light source apparatus 3B, an R LED lighting power source 80R, G LED lighting power source 80G and B LED lighting power source 8B corresponding respectively to the above mentioned LED 26R, 26G and 26B are provided and are connected respectively to the LED 26R, 26G and 26B of the above mentioned tip LED fitted electronic scope 2B through the above mentioned power source connector receptacle 76, power source connector 75 and cables 27R, 27G and 27B.

The above mentioned respective LED lighting power sources 80R, 80G and 80B are to be on respectively by the outputs of AND-gates 81R, 81G and 81B into which the driving signal from the control circuit 48 and the power source on/off signal from the scope discriminating circuit 44 are input. The above mentioned control circuit 48 will output driving signals sequentially to the above mentioned respective AND-gates 81R, 81G and 81B. Therefore, when the tip LED fitted electronic scope 2B is connected to the above mentioned connector receptacle 31, the respective LED lighting power sources 80R, 80G and 80B will sequentially operate to be on and the respective LEDs 26R, 26G and 26B will sequentially emit light to illuminate the object with frame sequential light of R, G and B.

A CCU 4B corresponding to the frame sequential type is provided within the above mentioned light source apparatus 3B. The video signal processing circuit 47B in this CCU 4B is formed as shown, for example, in FIG. 9.

That is to say, the signal read out of the CCD 18 will be amplified by a pre-amplifier 83, will then have a video signal extracted in a sample holding circuit, will be $\gamma$-corrected in a $\gamma$-correcting circuit 85, will be converted to a digital signal by an A/D converter 86, will be switched by a multiplexer 87 as synchronized with a color frame sequential illumination by the above mentioned rotary filter 79 or respective LED lighting power sources 80R, 80G and 8B and will be stored sequentially in frame memories 88R, 88G and 88B corresponding to the respective colors of R, G and B. These frame memories 88R, 88G and 88B will be simultaneously read out and will be converted respectively to analogue color signals R, G and B by a D/A converter 89. The above mentioned color signals R, G and B will be output as three primary color signals respectively through drivers 90. The above mentioned color signals R, G and B will be input into a matrix circuit 91 to produce a luminance signal Y and color difference signals R-Y and B-Y, will be further input into an NTSC encoder 92 to be converted to a composite video signal of the NTSC system and will be output.

Figure 10:
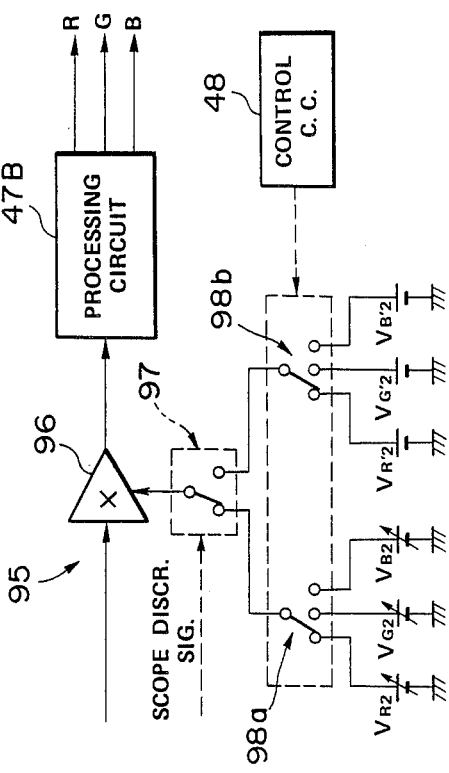

As in the first embodiment, an illuminating light spectral intensity correcting circuit 95 as is shown in FIG. 10 may be provided.

In this illuminating light spectral intensity correcting circuit 95, the output signals of the CCD 18 read out sequentially in response to the respective illuminating light of R, G and B input in time series into the video signal processing circuit 47B will be input into a multiplier 96 and the gain will be adjusted independently for each signal corresponding to each illuminating light by this multiplier 96. The multiplied amount setting terminal of the above mentioned multiplier 96 is connected to the fixed contact of a two-contact switching switch 97 and the switching contacts of this switching switch 97 are connected respectively to the respective fixed contacts of three-contact switching switches 98a and 98b. Variable voltage power sources $V_{R2}$, $V_{G2}$ and $V_{B2}$ and fixed voltage power sources $V_{R2'}$, $V_{G2'}$ and $V_{B2'}$ are connected respectively to the respective switching contacts of the above mentioned switching switch 98a and 98b. The above mentioned switching switch 97 is switched by the scope discriminating signal from the scope discriminating circuit 44 so that, when the tip LED fitted electronic scope 2B is connected, the switching switch 98a side will be selected and, when the LG fitted electronic scope 1B is connected, the switching switch 98b will be selected. The above mentioned switching switches 98a and 98b are controlled by the control circuit 42 and are switched as synchronized with a color frame sequential illumination so that the power sources $V_{R2}$, $V_{R2'}$, $V_{G2}$, $V_{G2'}$, $V_{B2}$ and $V_{B2'}$ may be sequentially selected and the gain may be set independently for each color. With the above mentioned LG fitted electronic scope 1B and tip LED fitted electronic scope 2B, the gain by the above mentioned multiplier 96 is switched by switching the switching switch 97.

The above mentioned power sources $V_{R2'}$, $V_{G2'}$ and $V_{B2'}$ may be also variable in the voltage.

Figure 11:
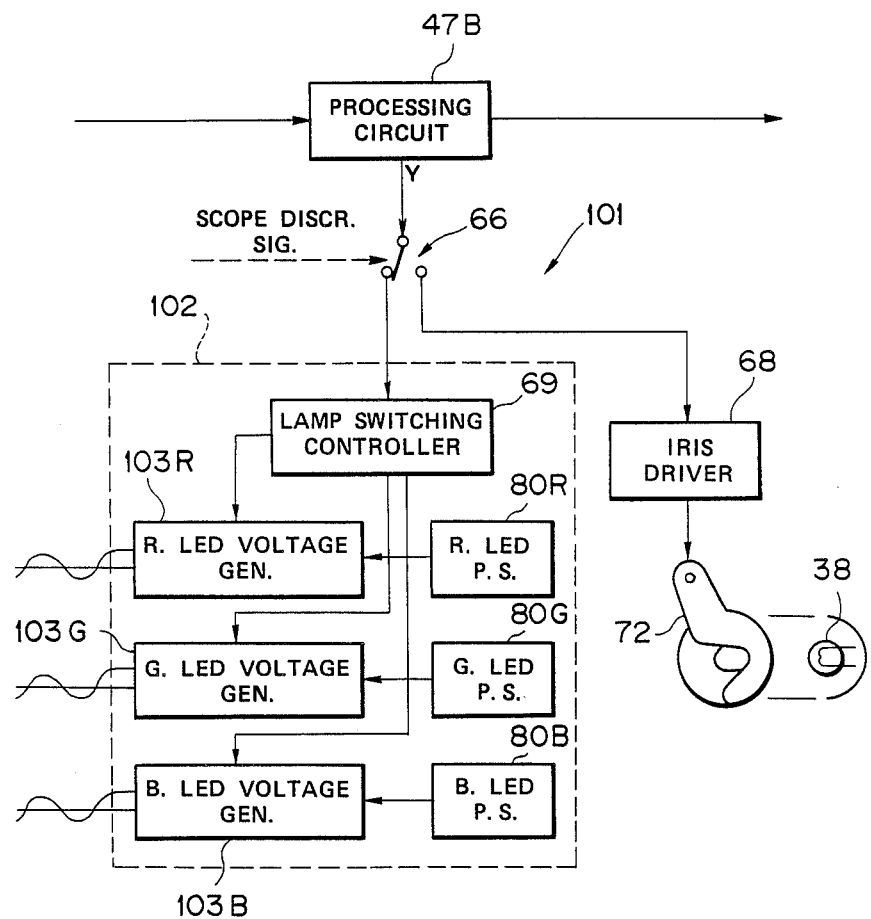

As in the first embodiment, a light adjusting circuit 101 as is shown, for example, in FIG. 11 may be provided.

In this light adjusting circuit 101, the luminance signal from the video signal processing circuit 47B is selectively input into the LED lighting circuit 102 and iris driving circuit 68 through the switching switch 66. The above mentioned switching switch 66 is switched by the scope discriminating signal from the scope discriminating circuit 44 so that, when the tip LED fitted electronic scope 2B is connected, the LED lighting circuit 102 side will be selected and, when the LG fitted electronic scope 1B is connected, the iris driving circuit 68 side will be selected.

The above mentioned LED lighting circuit 102 comprises a lighting time number controlling circuit 69 controlling the number of times of lighting the LED per unit time in response to the level of this luminance signal Y by inputting the above mentioned luminance signal Y, LED lighting power sources 80R, 80G and 80B for respective colors and LED lighting voltage generating circuits 103R, 103G and 103B connected respectively to the above mentioned respective LED lighting power source 80R, 80G and 80B, controlled by the above mentioned lighting time number controlling circuit 69 and generating a voltage in the form, for example, of pulses applied to the respective LED's 26R, 26G and 26B. As in the first embodiment, in the above mentioned lighting time number controlling circuit 69, when the level of the luminance signal Y is small, that is, when the image is dark, the lighting time number will be increased but, on the other hand, when the level of the luminance signal Y is large, that is, when the image is bright, the lighting time number will be decreased. Therefore, as shown in FIG. 6, the LED lighting voltage waveforms output from the above mentioned LED lighting voltage generating circuits 103R, 103G and 103B will be short pulses in the period when the image is dark but will be long pulses in the period when the image is bright. As shown in FIG. 7(a), the above mentioned respective LED lighting power sources 80R, 80G and 80B are controlled by the controller 48 through AND-gates 81R, 81G and 81B to operate to be on sequentially.

The other formations, operations and effects of this embodiment are the same as in the first embodiment.

FIGS. 12 to 14 show the third embodiment of the present invention.

In this embodiment, as shown in FIG. 12 (a), there is provided a light source apparatus 3C wherein the CCU 4A is removed from the the light source apparatus 3A in the first embodiment. An LG fitted filter scope 1C as is shown in FIG. 12 (b) and a tip LED fitted filter scope 2C as is shown in FIG. 12 (c) can be connected to this light source apparatus 3C.

In the above mentioned LG fitted fiber scope 1C, the tip surface of an image guide (IG) 111 consisting, for example, of a fiber bundle is arranged in the image forming position of the objective lens system 17 and this image guide 111 is inserted through the insertable part 11 to transmit an object image to the eyepiece part 112 side connected to the rear end of the operating part 12 so that the object image transmitted through the above mentioned image guide 111 may be observed through an eyepiece 113 from the above mentioned eyepiece part 112. The other formations are the same as in the LG fitted electronic scope 1A.

Also, in the above mentioned tip LED fitted fiber scope 2C, the as in the above mentioned LG fitted fiber scope 1C, the object image is transmitted through the image guide 111 so as to be observable from the eyepiece part 112. The other formations are the same as in the tip LED fitted electronic scope 2A.

Thus, in this embodiment, by providing one light source apparatus 3C, both of the LG fitted fiber scope 1C and tip LED fitted filter scope 2C can be used Further, an externally fitted television camera 115 as is shown in FIG. 13 can be connected to the eyepiece part 112 of each of the above mentioned filter scopes 1C and 2C to image the object image and is provided with an image forming lens 116 and a CCD 18 arranged in the image forming position of this image forming lens 116. For example, a color filter array is provided on the front surface of the above mentioned CCD 18. The above mentioned television camera 115 can be connected through the signal connector 21 to the signal connector receptacle 32 of the CCU 4A separated from the above mentioned light source apparatus 3C.

As shown in FIG. 14, the above mentioned LG fitted fiber scope 1C and tip LED fitted fiber scope 2C can be connected also to the light source apparatus 3A of the first embodiment. Also, the above mentioned television camera 115 can be connected to the above mentioned light source 3A. Therefore, by providing the above mentioned light source apparatus 3A, a naked eye observation by the fiber scopes 1C and 2C, a monitor observation by the electronic scopes 1A and 2A and a monitor observation by the fiber scopes 1C and 2C and television camera 115 are made possible.

The above mentioned electronic scopes 1A and 2A can be also used as connected to the above mentioned separate light source apparatus 3C and CCU 4A.

Figure 16:
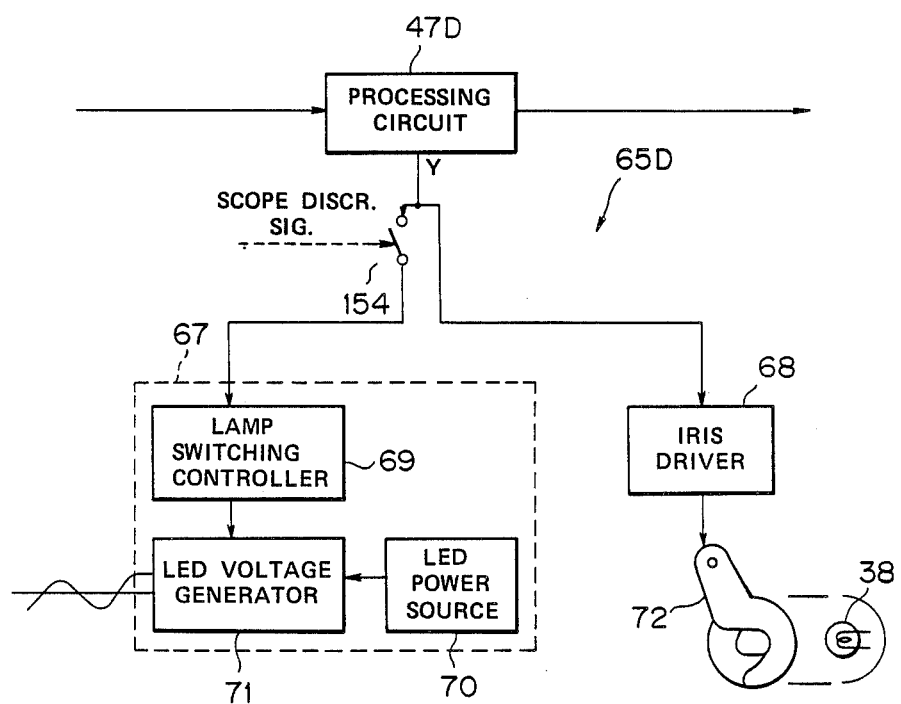

FIGS. 15 and 16 show the fourth embodiment of the present invention.

In this embodiment, a blue color light is fed by a light source apparatus 3D.

The tip LED and LG fitted electronic scope 2D in this embodiment is provided in the tip part 16 with a red color light emitting LED 26R and green color light LED 26G adjacently to which is provided the exit end surface of a blue color light guide 151 inserted through the insertable part 111. This blue color light guide 151 is inserted through the insertable part 11 and universal cord 13 and is connected to the light source connector 24 of the connector 14. This light source connector 24 is removably connected to the light source connector receptacle 33 of the light source apparatus 3D. The light emitted from the light source lamp 38 controlled in lighting by the lamp lighting circuit 37 will be condensed by the condenser lens 39 and will enter the entrance end surface of the blue color light guide 151 of the light source connector 24. Between this light source lamp 38 and condenser lens 39, a blue color monochromatic filter 153 is provided so as to be interposed in the light path of the illuminating light by a motor 152 and is to transmit only the blue color light.

When a discriminating signal from the scope discriminating circuit 44 is input, the above mentioned motor 152 will be driven.

When the tip LED and LG fitted electronic scope 2D is connected to the light source apparatus 3D and the switch 43 is on, the scope discriminating circuitry 44 will output a discriminating signal, for example, of an H level. This discriminating signal will be input into the LED lighting power source 41 and motor 152. In case a discriminating signal of an H level is input, the scope discriminating circuit 44 will drive the motor 152 to interpose the blue color monochromatic filter 153 in the light path and will feed a blue color light to the blue color light guide 151.

The light source apparatus 3D may be provided with a light adjusting circuit 65D as is shown in FIG. 16.

In the light adjusting circuit 65D, the luminance signal Y from the video signal processing circuit 470 will be input directly into the iris driving circuit 68 different from the first embodiment. The luminance signal Y will be branched to be input into a LED lighting circuit 67 through a switch 154. This LED lighting circuit 67 comprises a lighting time number controlling circuit 69 controlling the number of times of lighting the LED per unit time, an LED lighting power source 70 and an LED lighting voltage generating circuit 71 connected to the above mentioned LED lighting power source, controlled by the above mentioned lighting time number controlling circuit 69 and generating a voltage in the form, for example, of pulses applied to the LED 26R and 26G.

By the above mentioned lighting time number controlling circuit 69, when the level of the luminance signal Y is small, that is, when the image is dark, the lighting time number will be increased but, on the other hand, when the level of the luminance signal Y is large, that is, when the image is bright, the lighting time number will be decreased. Therefore, as shown in FIG. 6, the LED lighting voltage waveform output from the above mentioned LED lighting voltage generating circuit 71 will be of short pulses in the period when the image is dark but of long pulses in the period when the image is bright.

By the formation as in this embodiment, a color light requiring a large light amount can be fed by the light guide. In this embodiment a blue color light is fed by the light guide but such other color lights as of red and green may be fed by the light guide.

The other formations, operations and effects are the same as in this first embodiment.

Figure 17A:
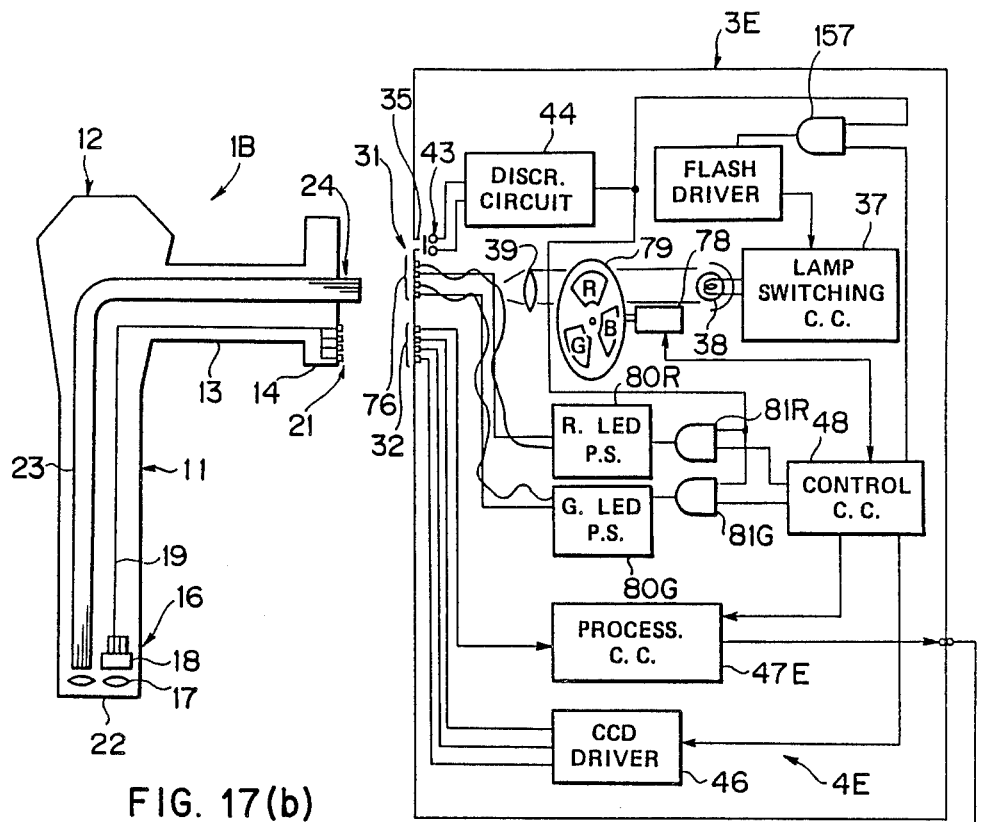
FIGS. 17 to 19 relate to the fifth embodiment of the present invention.
Figure 17B:
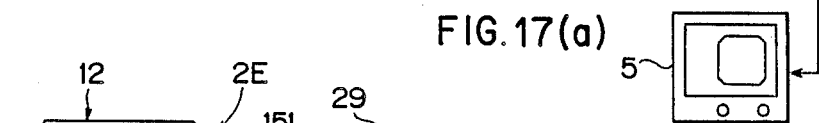
Figure 17C:
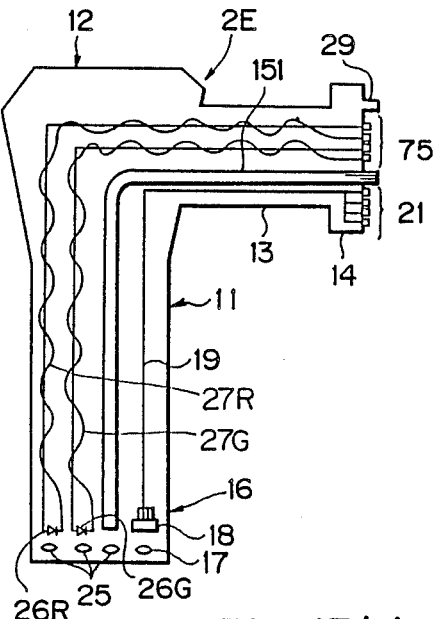
Figure 18:
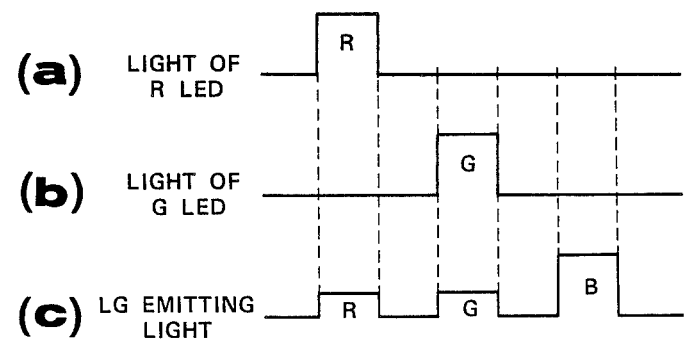
Figure 19:
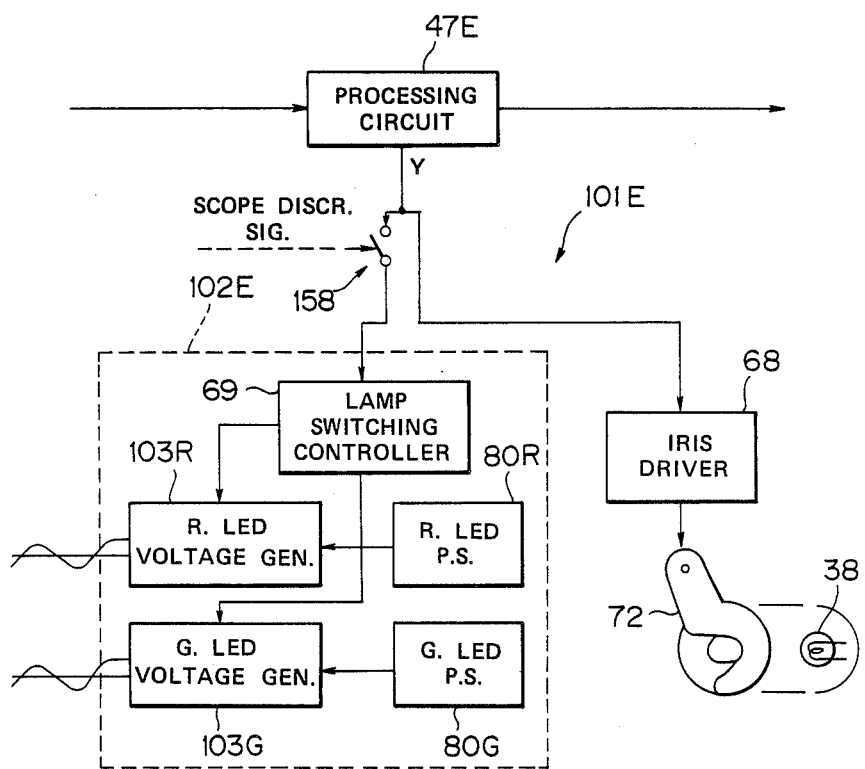

FIGS. 17 to 19 show the fifth embodiment of the present invention.

In this embodiment, the light source apparatus 3B corresponding to the frame sequential type of the second embodiment is provided with a flask driving circuit 156 so that, in case the rotary filter 79 transmits a blue color light, the light amount of the light source lamp 38 will be increased.

The tip LED and LG fitted electronic scope 2E in this embodiment is provided in the tip part 16 with a red color light emitting LED 26R and green color light emitting LED 26R and with the exit end surface of the blue color light guide 151 inserted through the insertable part adjacently to these respective LED 26R and 26G. This blue color light guide 151 is inserted through the insertable part 11 and universal cord 13 and is connected to the light source connector 24 of the connector 14. This light source connector 24 is to be removably connected to the light source connector receptacle 33 of the light source apparatus 3E. The white color light emitted from the light source lamp 38 controlled in lighting by the lamp lighting circuit 37 will be condensed by the condenser lens 39 and will enter the entrance end surface of the blue color light guide 151 of the light source connector 24. The rotary filter 79 rotated and driven by the motor 78 is arranged between the light source lamp 38 and condenser lens 39.

The above mentioned lamp lighting circuit 37 is to be fed with an electric power from the flash driving circuit 156. This flash driving circuit 156 is to increase or decrease the voltage fed to the lamp lighting circuit 37 by the output from an AND-gate 157.

The discriminating signal from the scope discriminating circuit 44 and the control signal from the control circuit 48 are to be input into the above mentioned AND-gate 157.

The light source apparatus 3E may be provided with a light adjusting circuit 101E as is shown in FIG. 19.

In this light adjusting circuit 101E, a luminance signal Y from a video signal processing circuit 47E will be input directly into the iris driving circuit 68 and will be further branched to be input into an LED lighting circuit 102E through a switching switch 158. The above mentioned switching switch 158 will be switched by the scope discriminating signal from the scope discriminating circuit 44 so that, when the tip LED and LG fitted electronic scope 2E is connected, the LED lighting circuit 102E side will be selected and will adjust the light amounts of the respective LED's together with the iris driving circuit 68 and, when the LG fitted electronic scope 1B is connected, the light amounts will be adjusted only by the iris driving circuit 68.

In case the LG fitted electronic scope 1B is connected to the light source apparatus 3E, the switch 43 will be off and thereby the scope discriminating circuit 44 will output a discriminating signal, for example, of an L level to the AND-gates 81R, 81G and 157. A control signal, for example, of an H level from the control circuit will be input into the AND-gate 157 which will input a signal of an L level into the flash driving circuit 156. When the signal of the L level is input, the flash driving circuit 156 will continuously feed a constant voltage to the lamp lighting circuit 37. The light source lamp 38 will be controlled by the lamp lighting circuit 37 to emit a constant light amount. The illuminating light emitted from this light source lamp 38 will be separated into respective color light of red (R), blue (B) and green (G) by the rotary filter 79 driving controlled by the control circuit 48 and will be fed in constant light amounts to the light guide 24.

In case the tip LED and LG fitted electronic scope 2E is connected, the switch 43 will be on and the scope discriminating circuit 44 will output a discriminating signal, for example, of an H level continuously to the AND-gates 81R, 81B and 157. The control circuit 48 will output a pulse-like control signal, for example, of an H level sequentially to the AND-gates 81R, 81B and 157. The control circuit 48 will control the drive of the motor 78 and will be synchronized to output a signal of an H level to the AND-gate 157 when the filter transmitting a blue color is interposed in the light path of the light source lamp 38. When the pulse-like signal from the control circuit 48 is input the AND-gates 81R, 81B and 157 will output signal of H levels respectively to the respective LED lighting power sources 80R and 80G and flash driving circuit.

When a signal of an H level is input, the flash driving circuit 156 will increase the voltage and will feed it to the lamp lighting circuit 37. As in FIGS. 18(a) and (b), the control circuit 48 will input a control signal of an H level sequentially into the respective LED power sources 80R and 80G to make the respective LED 26R and 26G emit light. Also, as in FIG. 18(c), the flash driving circuit 156 will be synchronized with the rotary filler 79 and will increase the light amount of only the blue color light.

By the formation as in this embodiment, a color light requiring a large light amount can be fed by the light guide. In this embodiment, a blue color light is fed by the light guide but such other light colors such as of red and green may be fed by the light guide.

The other formations, operations and effects are the same as in the second embodiment.

FIGS. 20 and 21 show the sixth embodiment of the present invention.

In this embodiment, the light source apparatus of the third embodiment is provided with the blue color monochromatic filter 153.

The same as in the above mentioned LG fitted fiber scope IC, in the tip LED fitted fiber scope 2F, an object image is transmitted by the image guide 111 so as to be observable from the eyepiece part 112. The other formations are the same as in the tip LED and LG fitted electronic scope 2D.

In the light source apparatus 3F, the CCU 4D is made separate from the light source apparatus 3D of the fourth embodiment but the other formations are the same as in the fourth embodiment.

By forming as in this embodiment, a color light requiring a large light amount can be fed by the light guide. In this embodiment<a blue color light is fed to the light guide but other light colors such as red and green may be fed by the light guide.

It is apparent that, in this invention, working modes different in a wide range can be formed on the basis of this invention without deviating from the spirit and scope of the invention. This invention is not restricted by its specific working mode except being limited by the appended claims.

The present invention is not limited to the above mentioned respective embodiments. For example, the light source internally provided within the endoscope is not limited to an LED but may be, for example, a lamp by tungten filaments or an EL device.

As explained above, according to the present invention, a light source feeding an illuminating light to the light guide and a power source feeding an electric power to the light source internally provided within the endoscope body are provided and therefore the endoscope light sources apparatus can be used in common by both of an endoscope having a light guide and an endoscope having a light source.

What is claimed is:

1. An endoscope apparatus comprising:
   a first endoscope having a light guide means which can transmit an illuminating light and can radiate said illuminating light onto an object and an observing means wherein an image of said object illuminated by said light guide means can be observed;
   a second endoscope having a light source which can emit a light of a single wavelength band and can radiate said light onto an object and an observing means wherein an image of said object can be observed;
   a light source apparatus having a light guide light source which can feed an illuminating light to said light guide means and a power source which can feed an electric power to said light source provided in said second endoscope and capable of being selectively connected with said first endoscope and said second endoscope.

2. An endoscope apparatus according to claim 1 wherein said light source of the second endoscope has three light emitting diodes which can emit light of different wavelength ranges.

3. An endoscope apparatus according to claim 1 wherein said second endoscope further has a light guide means which can transmit a light of a single wavelength range.

4. An endoscope apparatus according to claim 1 wherein said light source apparatus further has a scope discriminating means which can discriminate the connected endoscope and can output a signal which can control the light guide light source and power source.

5. An endoscope apparatus according to claim 1 wherein said power source is to feed an electric power to light emitting diodes.

6. An endoscope light source apparatus which can be selectively connected with a endoscope having a light guide means which can transmit an illuminating light for an object and an endoscope having a light source which can illuminate an object, comprising:
   a light guide light source which can feed an illuminating light to said light guide means; and
   a power source which can feed an electric power to said light source provided in said endoscope.

7. An endoscope light source apparatus according to claim 6 further comprising a scope discriminating means which can discriminate the connected endoscope and can control said light guide light source and power source.

* * * * *

UNITED STATES PATENT AND TRADEMARK OFFICE
CERTIFICATE OF CORRECTION

PATENT NO. : 4,884,133

DATED : November 28, 1989

INVENTOR(S) : KANNO et al

It is certified that error appears in the above-identified patent and that said Letters Patent is hereby corrected as shown below:

On the cover page, Item [75], after "Kazuhiko Ohzeki, Hachioji" the following should appear: --Yoshikazu Tojo, Hachioji; Shinichi Nishigaki, Tokyo; Hiromasa Suzuki, Akishima; Takeaki Nakamura, Hino--.

Signed and Sealed this

Ninth Day of July, 1991

*Attest:*

HARRY F. MANBECK, JR.

*Attesting Officer*     *Commissioner of Patents and Trademarks*